(12) United States Patent
Li et al.

(10) Patent No.: US 9,834,503 B2
(45) Date of Patent: Dec. 5, 2017

(54) METHOD FOR PREPARING IMINODISUCCINATE CHELATING AGENT

(71) Applicant: HEBEI THINK-DO ENVIRONMENT CO., LTD., Shijiazhuang (CN)

(72) Inventors: Wenxi Li, Shijiazhuang (CN); Zhenping Xing, Shijiazhuang (CN)

(73) Assignee: HEBEI THINK-DO ENVIRONMENT CO., LTD., Shijiazhuang, Hebei (CN)

( * ) Notice: Subject to any disclaimer, the term of this patent is extended or adjusted under 35 U.S.C. 154(b) by 0 days.

(21) Appl. No.: 15/129,001

(22) PCT Filed: Feb. 28, 2015

(86) PCT No.: PCT/CN2015/073394
§ 371 (c)(1),
(2) Date: Sep. 26, 2016

(87) PCT Pub. No.: WO2015/149599
PCT Pub. Date: Oct. 8, 2015

(65) Prior Publication Data
US 2017/0121277 A1    May 4, 2017

(30) Foreign Application Priority Data
Apr. 3, 2014   (CN) .......................... 2014 1 0131945

(51) Int. Cl.
C07C 227/18    (2006.01)
C07C 229/24    (2006.01)

(52) U.S. Cl.
CPC .......... *C07C 227/18* (2013.01); *C07C 229/24* (2013.01)

(58) Field of Classification Search
CPC ........................... C07C 227/18; C07C 229/24
See application file for complete search history.

(56) References Cited

U.S. PATENT DOCUMENTS 5,362,412 A * 11/1994 Hartman et al. ...... C07C 229/16
                                               252/186.25
7,166,688 B1 * 1/2007 Dean ..................... C07C 231/02
                                               528/354
7,183,429 B2 * 2/2007 Groth et al. ........... A01N 37/44
                                               562/571

FOREIGN PATENT DOCUMENTS

| CN | 1356308 A | 7/2002 |
|----|-----------|--------|
| CN | 1126733 C | 11/2003 |
| CN | 101683601 A | 3/2010 |
| GB | 1306331 A | 2/1973 |
| JP | H05329109 | * 5/1992 |

OTHER PUBLICATIONS

JPH05320109, Askaway Yoshiaki, Production of Iminodisuccinic acid metallic salt, 1992, English translation, 7 pages.*
Li Jing et al., Stabilizing Effect of Iminodisuccinic Acid on Metal Ions [J], Chinese Journal of Applied Chemistry, Mar. 2003, vol. 20, No. 3, 3 pages, Tianjin, China.
Wu Changyu et al., Synthesis of Iminoisuccinic Acid and Its Chelating Ability, Chemical Industry and Engineering, Mar. 31, 2007, vol. 24, No. 24, 4 pages, China.
Zhang Qi-peng et al., Synthesis and Properties Tests of Green Chelating Agent Iminodisuccinic Acid [J], Journal of Zhejiang Sci-Tech University, May 2009, vol. 26, No. 3, 6 pages, Hangzhou, China.
Su Xia-fei et al., Study on Synthesis and Properties of Iminodisuccinic Acid [J], Textile Auxiliaries, Jul. 2011, vol. 28, No. 7, 4 pages, Hangzhou, China.
Shi Ying-ying, Study on Synthesis and Purification of Iminodisuccinic Acid [J], Guangzhou Chemical Industry, Dec. 2013, vol. 41, No. 24, 4 pages, Guangzhou, China.
International Search Report for PCT/CN2015/073394 dated Jun. 5, 2015, 4 pages.

* cited by examiner

*Primary Examiner* — Yate K Cutliff
(74) *Attorney, Agent, or Firm* — Reising Ethington P.C.; Matthew J. Schmidt

(57) ABSTRACT

A method for preparing an iminodisuccinate chelating agent, wherein a reaction comprising raw material A, raw material B, an alkali metal hydroxide, and water is carried out under ambient pressure, and at a pH in the range of 6-12 and a reaction temperature ranging from 65° C. to a boiling reflux temperature, and the mixed liquid obtained after the reaction is a mixture containing the iminodisuccinate chelating agent. The raw material A is a compound capable of obtaining a maleate through alkaline hydrolysis; and the raw material B is a compound capable of obtaining an aspartic acid through alkaline hydrolysis. With mild reaction conditions, a short reaction time and a high reaction yield, the preparation method is able to shorten the production process, improve the production efficiency, and reduce the production cost, and it is truly a preparation method which is highly efficient, environmentally friendly, and extremely suitable for industrial scale production.

18 Claims, No Drawings

METHOD FOR PREPARING IMINODISUCCINATE CHELATING AGENT

TECHNICAL FIELD

This disclosure relates to a method for preparing metal chelating agents, more specifically for preparing iminodisuccinate chelating agent.

BACKGROUND

Chelating agents, also called complexing agents, are organic or inorganic compounds which can make heavy metal ions passivated through chelating with heavy metal ions and then forming a stable water-soluble complex. Chelating agents, containing electron donors to form coordinate bonds with heavy metal ions, are particularly effective in softening, descaling, rustproofing, stabilizing, synergism and so on. Therefore, chelating agents have been widely used in multiple technical fields such as water treatment, textile dying and papermaking, etc. According to their molecular structures, chelating agents can be roughly classified into groups including phosphate chelating agents, amino carboxylic acid chelating agents, hydroxy carboxylic acid chelating agents, organic phosphonic acid salt chelating agents and polycarboxylic acid chelating agents, etc.

Iminodisuccinate, a new-type amino carboxylic acid chelating agent, is extremely effective in chelating transition metal ions or alkali metal ions, particularly iron ions and copper ions, with its chelating power surpassing that of EDTA. Furthermore, in comparison to traditional common chelating agents such as phosphate, citric acid and EDTA, etc., iminodisuccinate chelating agents are readily biodegradable with excellent ecosystem compatibility, and have been considered as a true green chelating agent and gained wide market acceptance.

At present, LanXess in Germany has produced iminodisuccinate chelating agent in industrial scale and marketed it around the world. The production process of LanXess uses maleic anhydride and ammonia as the raw materials with pH of the reaction system later adjusted with the addition of sodium hydroxide and the reaction fulfilled under high temperature and high pressure, and eventually produces a mixed solution containing the iminodisuccinate chelating agent of over 70%. Unfortunately, high temperature and high pressure reaction adopted in this process not only poses huge potential safety hazards, but also puts stringent requirements in equipment selection, workshop design, space arrangement, production process management, etc. Thus, the production of iminodisuccinic acid salt with this process inherently is of high investment, high energy consumption, high cost and high risk. In addition, the use of ammonia in this process as the raw material will also unavoidably cause pollution to the environment and harm to the health of the operators.

Chinese patent CN1126733C also disclosed a method for preparing iminodisuccinate chelating agent. Still using maleic anhydride and ammonia as the raw materials, this method is claimed to be able to boost the yield of iminodisuccinate through controlling reaction system pH and enhance the conversion rate of maleic anhydride to over 97%. Unfortunately, the fulfilling of the reaction in this method also similarly needs the use of high temperature and high pressure, failing to address the issues of potential safety hazard and environmental pollution.

Wu Chang Yu, and etc. of Tianjin University (Wu Chang Yu, Wang Ya Quan and Li Jing, compound of green chelating agent iminodisuccinic acid salt and its chelation performance, chemical industry and project, March 2007, Vol. 24 No. 2) studied the preparation method of iminodisuccinic acid salt as well. They confirmed the optimal reaction conditions and speculated the reaction mechanism was that maleic acid and ammonia first created aspartic acid; then the aspartic acid further reacted with maleic acid and eventually generated iminodisuccinic acid. Furthermore, they briefly verified this proposed mechanism, and although it was confirmed that the reaction of aspartic acid and maleic acid as raw materials is able to produce iminodisuccinic acid salt, the reaction itself still requires the use of high pressure, and was not able to meet the requirements for industrialized production.

SUMMARY AND DETAILED DESCRIPTION

In at least some implementations, a synthetic method is disclosed that is suitable for the industrial scale production of iminodisuccinate chelating agent, and the method can be carried out at ambient pressure with high yield; but without the use of ammonia or ammonium hydroxide as raw material.

At least some implementations may utilize the following technical schemes:

A method for preparing an iminodisuccinate chelating agent, wherein a reaction comprising raw material A, raw material B, an alkali metal hydroxide, and water is carried out under ambient pressure, and at a pH in the range of 6-12 and a reaction temperature ranging from 65° C. to a boiling reflux temperature; wherein the mixed liquid obtained after the completion of the reaction is a mixture containing the iminodisuccinate chelating agent; and wherein the raw material A is a compound capable of generating a maleate through alkaline hydrolysis; and the raw material B is a compound capable of generating an aspartic acid through alkaline hydrolysis.

In at least some implementations, the preferred ratio of the reaction raw materials are, respectively, raw material A of 1 mole, raw material B of 0.8-1.2 moles, the alkali metal hydroxide of 2.0-5.5 moles, and water of 18-40 moles.

In at least some implementations, the more preferred ratio of the reaction raw materials are, respectively, raw material A of 1 mole, raw material B of is from 0.9-1.1 moles, the alkali metal hydroxide of 3.0-4.5 moles, and water of 20-25 moles.

In at least some implementations, the preferred pH of the reaction system is in a range of 9-12.

In at least some implementations, the preferred reaction temperature is from 95° C. to 120° C.

In at least some implementations, the preferred reaction time after reaching the reaction temperature is 6-30 hours.

In at least some implementations, the reaction include the followings specific steps: with stirring on, add water, the alkali metal hydroxide, the raw material A, and the raw material B in sequence to the reactor; mix well, heat up to 65° C. until reflux temperature, let the reaction run under ambient pressure for 6-30 hours; cool down to room temperature once the reaction is completed, and finally obtain a mixed solution containing the iminodisuccinate chelating agent.

In at least some implementations, the raw material A is selected from the group consisting of maleic anhydride, maleic acid, meleate, maleic acid derivatives, fumaric acid, fumarate, fumaric acid derivatives and mixtures thereof;

The raw material B is selected from the group consisting of L-aspartic acid, L-aspartate, L-aspartic acid derivatives, D-aspartic acid, D-aspartate, D-aspartic acid derivatives, D,L-hybrid configuration aspartic acid, D,L-hybrid configuration aspartate, D,L-hybrid configuration aspartic acid derivatives and mixtures thereof.

The alkali metal hydroxide is selected from the group consisting of lithium hydroxide, sodium hydroxide, potassium hydroxide and mixtures thereof.

In at least some implementations, the maleic acid derivatives is selected from the group consisting of maleic acid ester, maleic diamide, maleic oxalyl chloride and mixtures thereof; the fumaric acid derivatives is selected from the group consisting of fumaric acid ester, fumaric diamide, fumaric oxalyl chloride and mixtures thereof the L-aspartic acid derivatives is selected from the group consisting of L-aspartic ester, L-asparagine, L-aspartyl chlorine and mixtures thereof the D-aspartic acid derivatives is selected from the group consisting of D-aspartic ester, D-asparagine, D-aspartyl chlorine and mixtures thereof; the D,L-hybrid configuration aspartic acid derivatives is selected from the group consisting of D,L-hybrid configuration aspartic ester, D,L-hybrid configuration asparagines, D,L-hybrid configuration aspartyl chlorine and mixtures thereof.

In at least some implementations, the solid in the mixed solution obtained through the above mentioned method contains iminodisuccinic acid salt of 70%-85%.

In at least some implementations, a synthetic method is provided for the preparation of iminodisuccinate chelating agent under mild reaction condition with a short reaction time and a reaction high yield, simplified production process, improved production efficiency, and reduced production cost. It is truly a method which is highly efficient, environmentally friendly, and very suitable for industrialized mass production.

In at least some implementations, amino acid is used instead of ammonia or ammonium hydroxide, essentially removing the ammonification operation during the reaction, and completely avoiding environmental pollution and health hazards posed to the operators due to the evaporation of ammonia gas and potential safety risks associated with the storage of ammonia gas as well. Thus, this invention can enormously save costs associated with materials, equipment and etc. used to address safety and environmental concerns, greatly simplify the process of production management, production startup certification, safety evaluation and environmental impact assessment, etc. It is a fairly benign process for the industrial scale production of iminodisuccinate chelating agent.

In at least some implementations, a pH of 6-12, and more favorably 9-12 is used to control the rate of the reaction. Too high a pH will result in a very slow reaction rate. Lowering pH is able to speed up the reaction; but will also cause the increase in side reactions and the introduction of more impurities, negatively affecting the purity and color of the final product, and further limiting the eventual scope of its application. Therefore, according to this invention, the reaction system needs to be carefully controlled to ensure the reaction to occur at the specified pH range and ambient pressure, so, the raw materials can react at an acceptable rate to achieve the highest yield and best product quality.

In at least some implementations, material A of 1 mole, material B of 0.8-1.2 moles, alkali metal hydroxide of 2.0-5.5 moles, and water of 18-40 moles are used to ensure the reaction to occur smoothly at the selected concentration and pH. Since this preparation method doesn't use ammonia or ammonium hydroxide, there is no need to conduct follow-up ammonia distillation or any other caustic addition for pH adjustment after the finish of the reaction. Therefore, the addition of alkali metal hydroxide used for reaction and salt formation can be performed in one shoot, avoiding the caustic loss occurred during ammonia distillation and alkali addition steps in the ammonia or ammonium hydroxide based process, further making the reaction more controllable.

In at least some implementations, the charging sequence for the raw materials are: inject water and the alkali metal hydroxide to the reactor; mix well, then add raw material A and B. Blending water with the metal alkali metal hydroxide will ensure pH of the reaction system stay at a relative high level, further benefit the follow-up reactions after the addition of other materials. The reaction between the raw material A and the alkali metal hydroxide is a simple acid-base neutralization reaction. Once the reaction is finished, the pH of the reaction system will drop and become relative mild, from which further reactions with material B will benefit. This mild pH will effectively protect raw material B, an amino acid, from the destructive side reactions associated with the strong acid or alkali environments, further minimize the generation of impurities and ensure product yield and quality.

In at least some implementations, comprehensive control of the amount of each individual raw materials and pH of the reaction system enable the accomplishment of the reaction at ambient pressure and with only regular equipment, greatly improving production safety by eliminating risks associated with the use of pressurized vessels. The use of ambient pressure reactors instead of pressurized vessels will reduce the equipment investment by over 60% while at the same time, costs associated with relevant foundations for the equipment, auxiliary facilities, spatial arrangement for the equipment, and plant construction, etc. will also drop by over 50%. Since this invented process can thus be treated as a common chemical process, costs, efforts and time spent on construction declaration, safety evaluation, environmental assessment, operator training, production management, etc. will all be greatly reduced.

In at least some implementations, a one-step reaction method has been revealed, and follow-up steps such as caustic adjustment, heating up, ammonia distillation, cooling, etc. associated with the ammonia based method have all been eliminated, resulting in significantly shortened production time, greatly simplified production process, and noticeably reduced load for production. It is a process of great value for mass production. More importantly, this one-step reaction will not produce any exhaust gas, waste water, or any other wastes, and mixed solution obtained from the reaction can be sold as product for commercial use. It is a true clean chemical process.

EXAMPLES

Regents used in the examples are listed in the following table.

| Name | Manufacturer | Grade |
| --- | --- | --- |
| Cis-maleic anhydride | Shijiazhuang Bailong Chemical Co. | Purity 99% |
| Fumaric acid | Shijiazhuang Bailong Chemical Co. | Purity 99% |
| L-aspartic acid | Anhui Keyuan chemical Co. | |
| D-aspartic acid | Anhui Huaheng bioengineering Co. | |
| Sodium hydroxide aqueous solution | Shijiazhuang electrochemical factory | Purity 32% |

| Name | Manufacturer | Grade |
|---|---|---|
| Lithium hydroxide, Sodium Hydroxide, Potassium hydroxide | | Chemical grade |

This present invention revealed a method for preparing iminodisuccinate chelating agent: add all of the raw materials into reactor, then heat up and have the reaction run under ambient pressure, and once the reaction is finished, receive a mixed solution containing iminodisuccinate chelating agent.

Raw materials include raw material A, raw material B, alkali metal hydroxide and water. Raw material A, raw material B, alkali metal hydroxide are further specified respectively as in the following:

The raw material A is a compound capable of generating maleate through alkaline hydrolysis, and specifically it is selected from the group consisting of maleic anhydride, maleic acid, maleate, maleic acid derivatives, fumaric acid, fumarate, fumaric acid derivatives and mixtures thereof. More specifically, maleic acid derivatives is selected from the group consisting of maleic acid ester, maleic diamide, maleic oxalyl chloride and mixtures thereof; and fumaric acid derivatives is selected from the group consisting of fumaric acid ester, fumaric diamide, fumaric oxalyl chloride and mixtures thereof.

The raw material B is a compound capable of generating aspartic acid through alkaline hydrolysis; and specifically it is selected from the group consisting of L-aspartic, L-aspartate, L-aspartic derivatives, D-aspartic, D-aspartate, D-aspartic derivatives, D,L-hybrid configuration aspartic acid, D,L-hybrid configuration aspartate, D,L-hybrid configuration aspartic acid derivatives and mixtures thereof. More specifically, L-aspartic acid derivatives is selected from the group consisting of L-aspartic ester, L-asparagine, L-aspartyl chlorine and mixtures thereof; D-aspartic acid derivatives is selected from the group consisting of D-aspartic ester, D-asparagine, D-aspartyl chlorine and mixtures thereof; and D,L-aspartic acid derivatives is selected from the group consisting of D,L-aspartic ester mixture, D,L-asparagine mixture, D,L-aspartyl chlorine mixture and mixtures thereof;

Alkali metal hydroxide is selected from the group consisting of lithium hydroxide, sodium hydroxide, potassium hydroxide and mixtures thereof.

In at least some implementations, the preferred ratio of the reaction raw materials are, respectively, raw material A of 1 mole, raw material B of 0.8-1.2 moles, the alkali metal hydroxide of 2.0-5.5 moles, and water of 18-40 moles; and the more preferred ratio of the reaction raw materials are, respectively, raw material A of 1 mole, raw material B of is from 0.9-1.1 moles, the alkali metal hydroxide of 3.0-4.5 moles, and water of 20-25 moles.

In at least some implementations, the selected pH of the reaction system is 6-12, and more favorably 9-12;

The selected reaction temperature is 65° C. to boiling reflux temperature, and more preferably 95° C.-120° C.;

The reaction time is 6-30 hours.

In at least some implementations, the reaction include the followings specific steps: with stirring on, add water, the alkali metal hydroxide, the raw material A, and the raw material B in sequence to the reactor; mix well, heat up to 65° C. until reflux temperature, let the reaction run under ambient pressure for 6-30 hours; cool down to room temperature once the reaction is completed, and finally obtain a mixed solution containing the iminodisuccinate chelating agent.

In at least some implementations, the solid of the final mixed solution from the reaction is 30-50% with 70-85% of them is iminodisuccinic acid salt.

Example 1

Molar ratio of the raw materials is: raw material A (1.0); raw material B (1.0-1.1); alkali metal hydroxide (4.5-5.0); and water (20-25).

To a 2 L four-necked flask pre-charged with water of 5 g (0.28 mol), with stirring on, slowly add in sequence of the following: 32% sodium hydroxide solution of 973 g (including sodium hydroxide 7.78 mol, and water 36.76 mol), maleic anhydride of 159 g (1.62 mol), L-aspartic of 225 g (1.69 mol); In the whole charging process, adjust raw material charging speed and control temperature to no more than 65° C. After all raw materials are added, stir for 5 min until uniform, and at this stage, pH of the mixture is about 12. Then, heat the mixture up to 90±5° C. and maintain at this temperature for 28 hours for the reaction to occur. Once the reaction is finished, cool down to room temperature to receive a mixed solution with a solid of 43%, and 83% of the solid being tetrasodium iminodisuccinic acid.

Example 2

Molar ratio of the raw materials is: raw material A (1.0); raw material B (0.9-1.0); alkali metal hydroxide (5.0-5.5); and water (20-25).

To a 2 L four-necked flask pre-charged with water of 450 g (25 mol), with stirring on, slowly add in sequence of the following: potassium hydroxide of 291 g (5.2 mol), maleic acid ethyl ester of 144 g (1 mol), L-aspartic of 126 g (0.95 mol); In the whole charging process, adjust raw material charging speed and control temperature to no more than 65° C. After all raw materials are added, stir for 5 min until uniform, and at this stage, pH of the mixture is about 12. Then, heat the mixture up to 75±5° C. and maintain at this temperature for 19 hours for the reaction to occur. Once the reaction is finished, cool down to room temperature to receive a mixed solution with a solid of 53%, and 75% of the solid being tetrapotassium iminodisuccinic acid.

Example 3

Molar ratio of the raw materials is: raw material A (1.0); raw material B (1.1-1.2); alkali metal hydroxide (2.0-2.5); and water (20-25).

To a 2 L four-necked flask pre-charged with water of 360 g (20 mol), with stirring on, slowly add in sequence of the following: sodium hydroxide of 92 g (2.3 mol), maleic acid ammonium of 135 g (1 mol), L-aspartic sodium salt of 186 (1.2 mol). In the whole charging process, adjust raw material charging speed and control temperature to no more than 65° C. After all raw materials are added, stir for 5 min until uniform, and at this stage, pH of the mixture is about 10.8. Then, heat the mixture up to 100±5° C. and maintain at this temperature for 20 hours for the reaction to occur. Once the reaction is finished, cool down to room temperature to receive a mixed solution with a solid of 55%, and 73% of the solid being tetrasodium iminodisuccinic acid.

Example 4

Molar ratio of the raw materials is: raw material A (1.0); raw material B (0.9-1.0); alkali metal hydroxide (2.0-3.0); and water (35-40).

To a 2 L four-necked flask pre-charged with water of 550 g (30.6 mol), with stirring on, slowly add in sequence of the following: 32% sodium hydroxide solution of 250 g (including sodium hydroxide 2.0 mol, and water 9.4 mol), fumaric acid sodium salt of 128 g (1.0 mol), D,L-hybrid configuration aspartic acid of 120 g (0.9 mol). In the whole charging process, adjust raw material charging speed and control temperature to no more than 65° C. After all raw materials are added, stir for 5 min until uniform, and at this stage, pH of the mixture is about 9. Then, heat the mixture up to 90±5° C. and maintain at this temperature for 30 hours for the reaction to occur. Once the reaction is finished, cool down to room temperature to receive a mixed solution with a solid of 30%, and 70% of the solid being tetrasodium iminodisuccinic acid.

Example 5

Molar ratio of the raw materials is: raw material A (1.0); raw material B (0.8-1.0); alkali metal hydroxide (2.0-3.0); and water (18-20).

To a 2 L four-necked flask pre-charged with water of 648 g (36 mol), with stirring on, slowly add in sequence of the following: lithium hydroxide of 96 g (4.0 mol), fumaric acid of 232 g (2.0 mol), D-aspartic acid of 214 g (1.6 mol). In the whole charging process, adjust raw material charging speed and control temperature to no more than 65° C. After all raw materials are added, stir for 5 min until uniform, and at this stage, pH of the mixture is about 6. Then, heat the mixture up to 100±5° C. and maintain at this temperature for 6 hours for the reaction to occur. Once the reaction is finished, cool down to room temperature to receive a mixed solution with a solid of 45%, and 72% of the solid being tetralithium iminodisuccinic acid.

Example 6

Molar ratio of the raw materials is: raw material A (1.0); raw material B (1.0-1.1); alkali metal hydroxide (2.0-2.5); and water (25-30).

To a 2 L four-necked flask pre-charged with water of 450 g (25 mol), with stirring on, slowly add in sequence of the following: potassium hydroxide of 129 g (2.3 mol), fumaric acid potassium of 154 g (1 mol), D-aspartic potassium of 188 g (1.1 mol). In the whole charging process, adjust raw material charging speed and control temperature to no more than 65° C. After all raw materials are added, stir for 5 min until uniform, and at this stage, pH of the mixture is about 11. Then, heat the mixture up to 87±5° C. and maintain at this temperature for 26 hours for the reaction to occur. Once the reaction is finished, cool down to room temperature to receive a mixed solution with a solid of 50%, and 80% of the solid being tetrapotassium iminodisuccinic acid.

Example 7

Molar ratio of the raw materials is: raw material A (1.0); raw material B (0.9-1.0); alkali metal hydroxide (4.0-4.5); and water (20-25).

To a 2 L four-necked flask pre-charged with water of 414 g (23 mol), with stirring on, slowly add in sequence of the following: sodium hydroxide of 180 g (4.5 mol), maleic acid of 116 g (1 mol), L-aspartic dimethyl ester of 161 g (1 mol); In the whole charging process, adjust raw material charging speed and control temperature to no more than 65° C. After all raw materials are added, stir for 5 min until uniform, and at this stage, pH of the mixture is about 10. Then, heat the mixture up to reflux temperature and maintain at this temperature for 10 hours for the reaction to occur. Once the reaction is finished, cool down to room temperature to receive a mixed solution with a solid of 52%, and 85% of the solid being tetrasodium iminodisuccinic acid.

Example 8

Molar ratio of the raw materials is: raw material A (1.0); raw material B (1.1-1.2); alkali metal hydroxide (5.0-5.5); and water (25-30).

To a 2 L four-necked flask pre-charged with water of 540 g (30 mol), with stirring on, slowly add in sequence of the following: lithium hydroxide of 132 g (5.5 mol), fumaric acid dimethyl ester of 144 g (1.0 mol), L-asparagine of 152 g (1.15 mol); In the whole charging process, adjust raw material charging speed and control temperature to no more than 65° C. After all raw materials are added, stir for 5 min until uniform, and at this stage, pH of the mixture is about 12. Then, heat the mixture up to 65-75° C. and maintain at this temperature for 25 hours for the reaction to occur. Once the reaction is finished, cool down to room temperature to receive a mixed solution with a solid of 48%, and 78% of the solid being tetralithium iminodisuccinic acid.

Example 9

Molar ratio of the raw materials is: raw material A (1.0); raw material B (1.0-1.1); alkali metal hydroxide (3.0-3.5); and water (30-35).

To a 2 L four-necked flask pre-charged with water of 630 g (35 mol), with stirring on, slowly add in sequence of the following: potassium hydroxide of 168 g (3.0 mol), maleic acid amide of 115 g (1.0 mol), D-aspartic potassium of 180 g (1.05 mol); In the whole charging process, adjust raw material charging speed and control temperature to no more than 65° C. After all raw materials are added, stir for 5 min until uniform, and at this stage, pH of the mixture is about 8. Then, heat the mixture up to 110-120° C. and maintain at this temperature for 15 hours for the reaction to occur. Once the reaction is finished, cool down to room temperature to receive a mixed solution with a solid of 42%, and 84% of the solid being tetrapotassium iminodisuccinic acid.

The present disclosure has only listed 9 implementations as mentioned above. However, in view of this disclosure, persons or ordinary skill in this art will recognize further developments and modifications based on these implementations with the listed raw material A, raw material B, and alkali metal hydroxide, all of which are within the intended scope of this disclosure as set forth in the following claims. Through fine-tuning the molar ratio of the listed four raw materials and selecting reaction temperature and time relevant to the selected reaction system, one can similarly achieve at least some of the objectives described herein, and produce solution of iminodisuccinic acid salt of good quality.

The invention claimed is:
1. A method for preparing an iminodisuccinate chelating agent comprising:
providing raw materials including raw material A, raw material B, an alkali metal hydroxide, and water;

reacting the raw materials without addition of ammonia or ammonium hydroxide under ambient pressure, at a pH in the range of 6-12 and at a reaction temperature ranging from 65° C. to a boiling reflux temperature to obtain a solution comprising the iminodisuccinate chelating agent, wherein the raw material A is a compound capable of generating a maleate through alkaline hydrolysis, and the raw material B is a compound capable of generating an aspartic acid through alkaline hydrolysis.

2. The method for preparing an iminodisuccinate chelating agent according to claim 1, wherein the raw materials are reacted in the following ratio: raw material A of 1 mole, raw material B of 0.8-1.2 moles, the alkali metal hydroxide of 2.0-5.5 moles, and water of 18-40 moles.

3. The method for preparing an iminodisuccinate chelating agent according to claim 2, wherein the raw materials are reacted in the following ratio: raw material A of 1 mole, raw material B of 0.9-1.1 moles, the alkali metal hydroxide of 3.0-4.5 moles, and water of 20-25 moles.

4. The method for preparing an iminodisuccinate chelating agent according to claim 1, wherein the reaction temperature is from 95° C. to 120° C.

5. The method for preparing an iminodisuccinate chelating agent according to claim 1, wherein after reaching the reaction temperature, the raw materials are reacted for 6 to 30 hours.

6. The method for preparing an iminodisuccinate chelating agent according to claim 1, wherein the raw materials are provided in the form of a mixture, and wherein the mixture is prepared by mixing the raw materials together in the following sequence: the water, the alkali metal hydroxide, the raw material A, and then the raw material B.

7. The method for preparing an iminodisuccinate chelating agent according to claim 1, wherein:
the raw material A is selected from the group consisting of maleic anhydride, maleic acid, meleate, maleic acid derivatives, fumaric acid, fumarate, fumaric acid derivatives and mixtures thereof;
the raw material B is selected from the group consisting of L-aspartic acid, L-aspartate, L-aspartic acid derivatives, D-aspartic acid, D-aspartate, D-aspartic acid derivatives, D,L-hybrid configuration aspartic acid, D,L-hybrid configuration aspartate, D,L-hybrid configuration aspartic acid derivatives and mixtures thereof; and
the alkali metal hydroxide is selected from the group consisting of lithium hydroxide, sodium hydroxide, potassium hydroxide and mixtures thereof.

8. The method for preparing an iminodisuccinate chelating agent according to claim 7, wherein the maleic acid derivatives is selected from the group consisting of maleic acid ester, maleic diamide, maleic oxalyl chloride and mixtures thereof; the fumaric acid derivatives is selected from the group consisting of fumaric acid ester, fumaric diamide, fumaric oxalyl chloride and mixtures thereof; the L-aspartic acid derivatives is selected from the group consisting of L-aspartic ester, L-asparagine, L-aspartyl chlorine and mixtures thereof; the D-aspartic acid derivatives is selected from the group consisting of D-aspartic ester, D-asparagine, D-aspartyl chlorine and mixtures thereof; the D,L-hybrid configuration aspartic acid derivatives is selected from the group consisting of D,L-hybrid configuration aspartic ester, D,L-hybrid configuration asparagine, D,L-hybrid configuration aspartyl chlorine and mixtures thereof.

9. The method for preparing an iminodisuccinate chelating agent according to claim 1, wherein the solution comprises a solid that contains 70% to 85% of an alkali metal salt of iminodisuccinic acid.

10. The method for preparing an iminodisuccinate chelating agent according to claim 2, wherein:
the raw material A is selected from the group consisting of maleic anhydride, maleic acid, meleate, maleic acid derivatives, fumaric acid, fumarate, fumaric acid derivatives and mixtures thereof;
the raw material B is selected from the group consisting of L-aspartic acid, L-aspartate, L-aspartic acid derivatives, D-aspartic acid, D-aspartate, D-aspartic acid derivatives, D,L-hybrid configuration aspartic acid, D,L-hybrid configuration aspartate, D,L-hybrid configuration aspartic acid derivatives and mixtures thereof; and
the alkali metal hydroxide is selected from the group consisting of lithium hydroxide, sodium hydroxide, potassium hydroxide and mixtures thereof.

11. The method for preparing an iminodisuccinate chelating agent according to claim 3, wherein:
the raw material A is selected from the group consisting of maleic anhydride, maleic acid, meleate, maleic acid derivatives, fumaric acid, fumarate, fumaric acid derivatives and mixtures thereof;
the raw material B is selected from the group consisting of L-aspartic acid, L-aspartate, L-aspartic acid derivatives, D-aspartic acid, D-aspartate, D-aspartic acid derivatives, D,L-hybrid configuration aspartic acid, D,L-hybrid configuration aspartate, D,L-hybrid configuration aspartic acid derivatives and mixtures thereof; and
the alkali metal hydroxide is selected from the group consisting of lithium hydroxide, sodium hydroxide, potassium hydroxide and mixtures thereof.

12. The method for preparing an iminodisuccinate chelating agent according to claim 4, wherein:
the raw material A is selected from the group consisting of maleic anhydride, maleic acid, meleate, maleic acid derivatives, fumaric acid, fumarate, fumaric acid derivatives and mixtures thereof;
the raw material B is selected from the group consisting of L-aspartic acid, L-aspartate, L-aspartic acid derivatives, D-aspartic acid, D-aspartate, D-aspartic acid derivatives, D,L-hybrid configuration aspartic acid, D,L-hybrid configuration aspartate, D,L-hybrid configuration aspartic acid derivatives and mixtures thereof; and
the alkali metal hydroxide is selected from the group consisting of lithium hydroxide, sodium hydroxide, potassium hydroxide and mixtures thereof.

13. The method for preparing an iminodisuccinate chelating agent according to claim 5, wherein:
the raw material A is selected from the group consisting of maleic anhydride, maleic acid, meleate, maleic acid derivatives, fumaric acid, fumarate, fumaric acid derivatives and mixtures thereof;
the raw material B is selected from the group consisting of L-aspartic acid, L-aspartate, L-aspartic acid derivatives, D-aspartic acid, D-aspartate, D-aspartic acid derivatives, D,L-hybrid configuration aspartic acid, D,L-hybrid configuration aspartate, D,L-hybrid configuration aspartic acid derivatives and mixtures thereof; and the alkali metal hydroxide is selected from the group consisting of lithium hydroxide, sodium hydroxide, potassium hydroxide and mixtures thereof.

14. The method for preparing an iminodisuccinate chelating agent according to claim 6, wherein:
the raw material A is selected from the group consisting of maleic anhydride, maleic acid, meleate, maleic acid derivatives, fumaric acid, fumarate, fumaric acid derivatives and mixtures thereof;
the raw material B is selected from the group consisting of L-aspartic acid, L-aspartate, L-aspartic acid derivatives, D-aspartic acid, D-aspartate, D-aspartic acid derivatives, D,L-hybrid configuration aspartic acid, D,L-hybrid configuration aspartate, D,L-hybrid configuration aspartic acid derivatives and mixtures thereof; and
the alkali metal hydroxide is selected from the group consisting of lithium hydroxide, sodium hydroxide, potassium hydroxide and mixtures thereof.

15. The method for preparing an iminodisuccinate chelating agent according to claim 10, wherein the maleic acid derivatives is selected from the group consisting of maleic acid ester, maleic diamide, maleic oxalyl chloride and mixtures thereof; the fumaric acid derivatives is selected from the group consisting of fumaric acid ester, fumaric diamide, fumaric oxalyl chloride and mixtures thereof; the L-aspartic acid derivatives is selected from the group consisting of L-aspartic ester, L-asparagine, L-aspartyl chlorine and mixtures thereof; the D-aspartic acid derivatives is selected from the group consisting of D-aspartic ester, D-asparagine, D-aspartyl chlorine and mixtures thereof; the D,L-hybrid configuration aspartic acid derivatives is selected from the group consisting of D,L-hybrid configuration aspartic ester, D,L-hybrid configuration asparagine, D,L-hybrid configuration aspartyl chlorine and mixtures thereof.

16. The method for preparing an iminodisuccinate chelating agent according to claim 12, wherein the maleic acid derivatives is selected from the group consisting of maleic acid ester, maleic diamide, maleic oxalyl chloride and mixtures thereof; the fumaric acid derivatives is selected from the group consisting of fumaric acid ester, fumaric diamide, fumaric oxalyl chloride and mixtures thereof; the L-aspartic acid derivatives is selected from the group consisting of L-aspartic ester, L-asparagine, L-aspartyl chlorine and mixtures thereof; the D-aspartic acid derivatives is selected from the group consisting of D-aspartic ester, D-asparagine, D-aspartyl chlorine and mixtures thereof; the D,L-hybrid configuration aspartic acid derivatives is selected from the group consisting of D,L-hybrid configuration aspartic ester, D,L-hybrid configuration asparagine, D,L-hybrid configuration aspartyl chlorine and mixtures thereof.

17. The method for preparing an iminodisuccinate chelating agent according to claim 13, wherein the maleic acid derivatives is selected from the group consisting of maleic acid ester, maleic diamide, maleic oxalyl chloride and mixtures thereof; the fumaric acid derivatives is selected from the group consisting of fumaric acid ester, fumaric diamide, fumaric oxalyl chloride and mixtures thereof; the L-aspartic acid derivatives is selected from the group consisting of L-aspartic ester, L-asparagine, L-aspartyl chlorine and mixtures thereof; the D-aspartic acid derivatives is selected from the group consisting of D-aspartic ester, D-asparagine, D-aspartyl chlorine and mixtures thereof; the D,L-hybrid configuration aspartic acid derivatives is selected from the group consisting of D,L-hybrid configuration aspartic ester, D,L-hybrid configuration asparagine, D,L-hybrid configuration aspartyl chlorine and mixtures thereof.

18. A method for preparing an iminodisuccinate chelating agent comprising:
providing raw materials including raw material A, raw material B, an alkali metal hydroxide, and water, wherein the raw material A is a compound capable of generating a maleate through alkaline hydrolysis and the raw material B is a compound capable of generating an aspartic acid through alkaline hydrolysis; and
reacting the raw materials without addition of ammonia or ammonium hydroxide under ambient pressure to obtain a solution having a solids content in the range of 30% to 50%, wherein the solids content comprises 70% to 85% of an alkali metal salt of iminosuccinic acid.

* * * * *